United States Patent
Falahee

(10) Patent No.: US 8,128,666 B2
(45) Date of Patent: Mar. 6, 2012

(54) LOW PROFILE SCREW ANCHOR WITH VARIABLE AXIS/ANGLE FIXATION

(75) Inventor: Mark H. Falahee, Ann Arbor, MI (US)

(73) Assignee: Medical Designs, LLC, Ann Arbor, MI (US)

( * ) Notice: Subject to any disclaimer, the term of this patent is extended or adjusted under 35 U.S.C. 154(b) by 2275 days.

(21) Appl. No.: 10/807,999

(22) Filed: Mar. 24, 2004

(65) Prior Publication Data

US 2004/0193157 A1    Sep. 30, 2004

Related U.S. Application Data

(60) Provisional application No. 60/456,866, filed on Mar. 24, 2003.

(51) Int. Cl.
*A61B 17/58* (2006.01)
(52) U.S. Cl. .................. 606/273; 606/264
(58) Field of Classification Search .......... 606/61, 606/72, 273, 264
See application file for complete search history.

(56) References Cited

U.S. PATENT DOCUMENTS

| | | | | |
|---|---|---|---|---|
| 324,768 | A * | 8/1885 | Hunt | 411/358 |
| 1,091,674 | A * | 3/1914 | Lee | 411/176 |
| 4,648,388 | A * | 3/1987 | Steffee | 606/61 |
| 5,127,912 | A * | 7/1992 | Ray et al. | 606/61 |
| 5,380,324 | A * | 1/1995 | Muller et al. | 606/61 |
| 5,382,248 | A * | 1/1995 | Jacobson et al. | 606/60 |
| 5,476,463 | A * | 12/1995 | Boachie-Adjei et al. | 606/61 |
| 5,593,407 | A * | 1/1997 | Reis | 606/61 |
| 6,280,443 | B1 * | 8/2001 | Gu et al. | 606/61 |
| 6,423,067 | B1 * | 7/2002 | Eisermann | 606/65 |

* cited by examiner

*Primary Examiner* — Pedro Philogene
(74) *Attorney, Agent, or Firm* — Gifford, Krass, Sprinkle, Anderson & Citkowski, P.C.

(57) ABSTRACT

A low-profile bone anchoring system particularly suited to pelvis fixation in conjunction with spinal correction. The preferred embodiment utilizes screw fixation, followed by deployment of penetrating anchoring arms, expansion of outer sleeve, or both. The proximal ends of the screw anchors are preferably flush or deep to the bone surface. An internal screw mechanism is utilized to deploy side anchoring arms, or expansion of outer sleeve, or both. Serrated top edge interfaces with low profile variable axis/angled elbow (VAE), which has varying lengths/dimensions to accommodate anatomy and differing rod sizes. The VAEs preferably feature a serrated bottom edge to interface with anchor screw. Locking screw at elbow secures into inner threads of pelvis anchor screw. Each VAE captures a rod, end to end, or by passing rod through the side of elbow.

5 Claims, 2 Drawing Sheets

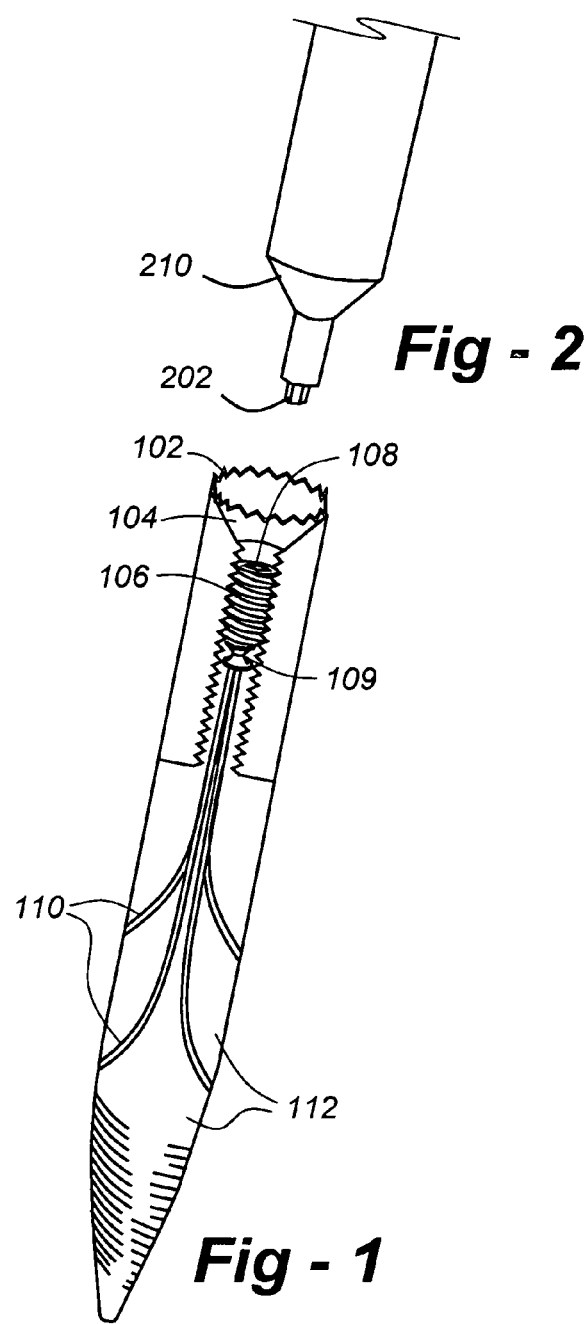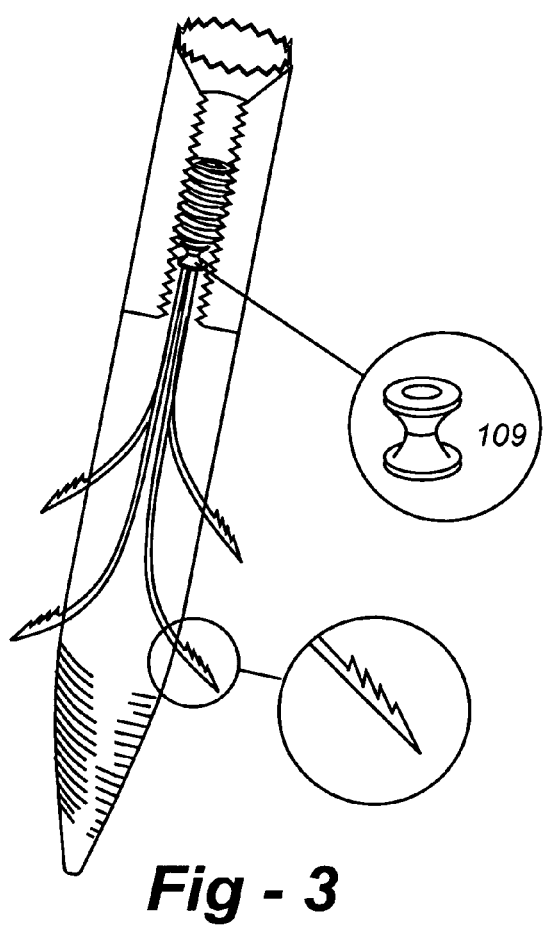

LOW PROFILE SCREW ANCHOR WITH VARIABLE AXIS/ANGLE FIXATION

REFERENCE TO RELATED APPLICATION

This application claims priority from U.S. Provisional Patent Application Ser. No. 60/456,866, filed Mar. 24, 2003, the entire content of which is incorporated herein by reference.

FIELD OF THE INVENTION

This invention relates generally to bone anchoring and, in particular, to a low-profile anchor system, particularly suited to pelvis fixation.

BACKGROUND OF THE INVENTION

Scoliosis is a condition that affects many children, teenagers, and adults. Broadly speaking, scoliosis is a condition whereby the human spine departs from its natural curvatures which help the body to move and remain flexible. There are several "warning signs" to determine if someone has scoliosis, including shoulders at different heights; one shoulder blade more prominent than the other; the appearance of a prominent hip; leaning of the entire body to one side; and other physical signs.

There are various treatment options for scoliosis, both non-surgical and surgical. Surgery is an option used primary for several scoliosis (i.e., curves greater than 45°, or for curves that do not respond to bracing.

The need remains, however, for improved techniques that provide stabilization, preferably without pronounced evidence of instrumentation. Such techniques may be particularly adaptable to neuromuscular scoliosis (cerebral palsy) requiring corrective rod fixation and stabilization to the pelvis in children/young adults with significant deformity and poor muscle mass protection.

SUMMARY OF THE INVENTION

This invention improves upon the prior art by providing a low-profile bone anchoring system particularly suited to pelvis fixation in conjunction with spinal correction. The preferred embodiment utilizes screw fixation, followed by deployment of penetrating anchoring arms, expansion of outer sleeve, or both.

The proximal ends of the screw anchors are preferably flush or deep to the bone surface. An internal screw mechanism is utilized to deploy side anchoring arms, or expansion of outer sleeve, or both. Serrated top edge interfaces with low profile variable axis/angled elbow (VAE), which has varying lengths/dimensions to accommodate anatomy and differing rod sizes.

The VAEs preferably feature a serrated bottom edge to interface with anchor screw. Locking screw at elbow secures into inner threads of pelvis anchor screw. Each VAE captures a rod, end to end, or by passing rod through the side of elbow. Small locking screws secure rod to elbow.

BRIEF DESCRIPTION OF THE DRAWINGS

FIG. 1 is a drawing of a preferred embodiment of the present invention, in particular cross-section;

FIG. 2 that shows an instrument to deploy side-arm anchors;

FIG. 3 is a drawing which shows the anchors deployed;

DETAILED DESCRIPTION OF THE INVENTION

Figure 5:
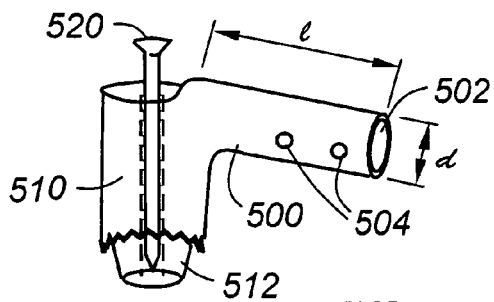
FIG. 5 is a drawing of a first rod-capture elbow according to the invention.

This invention is directed to a low-profile screw anchor system, facilitating variable axis and angle fixation to the pelvis, particularly for corrective rod fixation and stabilization of the type used to correct deformities, such as scoliosis. The invention covers different aspects, including implants and instrumentation. In terms of implants, the invention provides for an in-situ deployable pelvis screw anchor, and different styles of variable-axis elbows that connect the anchors to a rod system. In terms of instrumentation, an inventive inner core screw driver is used.

FIG. 1 is a drawing which shows a pelvis screw anchor according to the invention in partial cross-section. The device includes a top edge 102 which is preferably serrated around a tapered opening 104 providing access to an inner core screw plug 106.

The inner core screw plug 106 is, in turn, coupled to one or more deployable side anchors 110, which emerge from the sides of the device during deployment, as best seen in FIG. 3.

The body of the device of FIG. 1 is preferably threaded and tapered at 112, as shown. As with other components described herein, the device of FIG. 1 may be provided with in varying diameters, lengths, and tapering, to suit different applications.

The anchor of FIG. 1 is installed into bone, such as the tables of iliac crest, and other portions of the pelvis or other bones, depending upon the type of fixation. In practice, a pilot hole is drilled into the bone, and the device of FIG. 1 is either screwed into position or tapped into position, depending upon the dimensions of the components used. Once implanted, the inner core screwdriver of FIG. 2 is used. This device preferably includes an end 202 that engages with the inner core screw plug 106, and a tapering 210, which engages with the taper 104 of the screw anchor, thereby acting as a stop. The instrument of FIG. 2 is inserted into the screw anchor, and the device is turned, causing the plug 106 to advance distally which, in turn, causes the side anchors 110 to extend out from the side of the anchor, as shown in FIG. 3. In the preferred embodiment, a coupling 109 is not rigidly attached to either the advancing plug or side anchors, allowing for 360° spin as the plug is advanced. Also in the preferred embodiments, the ends of the side anchors 110 are serrated, as shown in FIG. 3.

Figure 4:
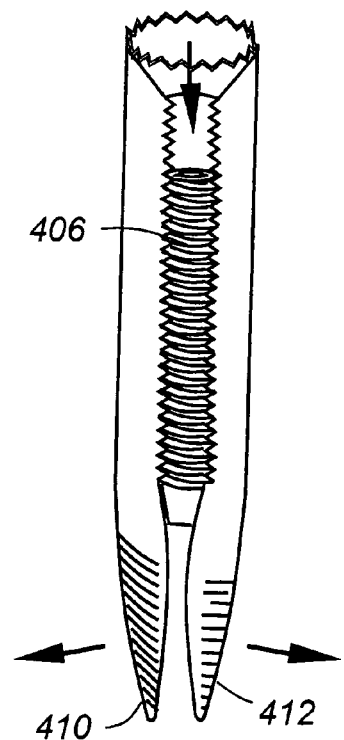
FIG. 4 is a drawing of an alternative embodiment of pelvis screw anchor according to the invention.

As an alternative to the penetrating side anchors discussed with reference to FIGS. 1 and 3, one or more outer advancing sleeves may be used, as shown in FIG. 4. In the case, a tool similar or identical that shown in FIG. 2 is used to advance a plug 406 which, in turn, advances one or more tangs 410, 412 outwardly, thereby providing for fixation and manner.

Once a pelvis screw anchor according to the invention is in place, a device used to couple the screw anchor to a rod system is attached between the anchor and associated rod. FIG. 5 shows one type of elbow, having an end 502 which receives a rod, which is then tightened by locking screws 504. For versatility, the diameter of the device of FIG. 5, d, as well as the length of the device of FIG. 5, l, are both provided in different sizes. The anchor-engaging portion of the device, 510, includes at tapered inner sleeve 512, and a serrated edge which locks to the anchor screw, as a fastener 520 is advanced and engaged into the hole on the proximal end 108 of the advancing plug 106 (or 406). As with other variable dimensions, the angle formed between the axis of the rod-receiving 500, and axis through locking screw 520 may also be provided in different sizes to suit different patient physiologies.

Figure 6:
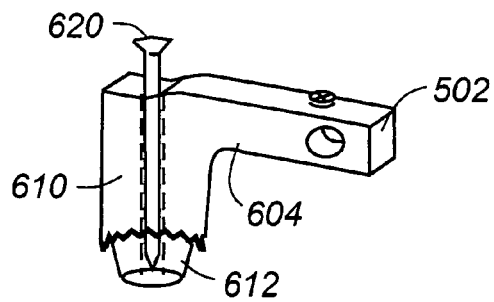
FIG. 6 is a drawing of a second style of rod-capture interface according to the invention.

FIG. 6 is a drawing which shows an alternative embodiment, wherein the rod-capture portion 602 is transverse to the rod-receiving end 604. Although an angle of 90° between the rod and bone 604 is shown, different angles may be used. Once the rod is in position, the tightening screw 610 locks the system in position. Otherwise, the use of a locking screw 620, serrated end 610 and tapered sleeve 612 are similar, if not identical, to the like features of FIG. 5.

Figure 7:
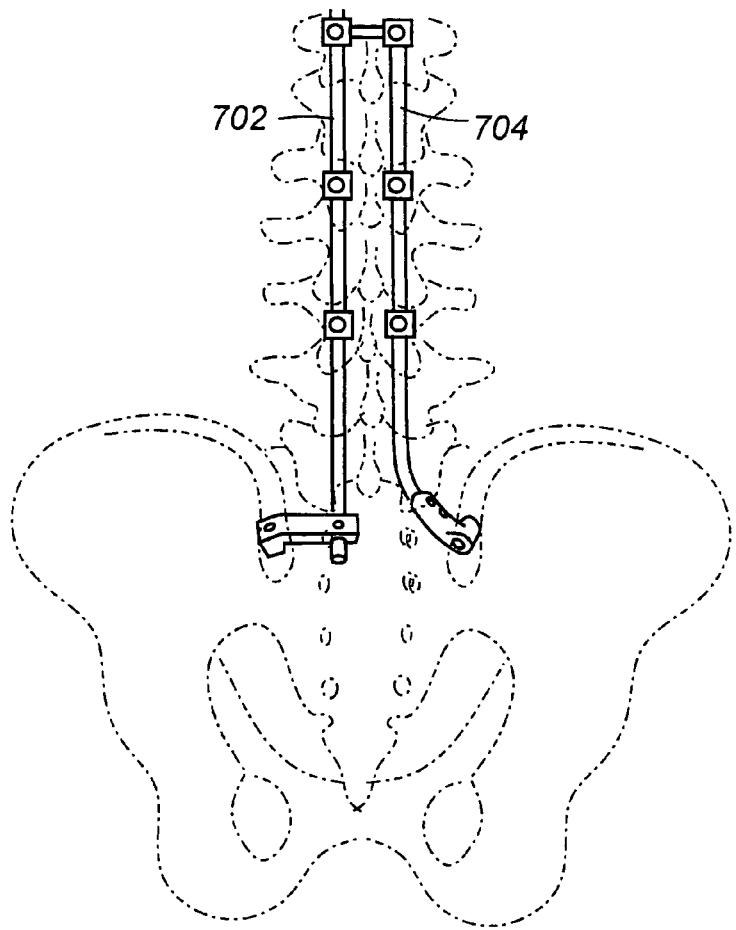
FIG. 7 is a drawing which shows a pair of pelvis screw anchors according to the invention, each being attached to a different style of variable-axis elbow, also provided according to the invention.

FIG. 7 is a drawing which shows a system in place for spinal fixation, including a pair of rods 702, 704, attached to multiple vertebral levels using pedicle screws or other devices not necessarily included in this invention. At the left of FIG. 7, a pelvic anchor is fixed between the tables of iliac crest, and a mechanism shown in FIG. 6 is used to engage with rod 702. At the right in FIG. 7, the pelvic anchor is placed below the plane of the pelvic wings, in which case the device of FIG. 5 is more appropriately utilized. Notre that although the rod 704 is bent to be received by the device of FIG. 5, the bend may be more or less pronounced, again, depending upon patient anatomy.

I claim:

1. An orthopaedic fixation system, comprising:
   a bone anchor having proximal and distal ends and wherein the proximal end is substantially at the surface of a bone once in position; and
   an elbow having portion that engages with the bone anchor once in position and an arm that engages with an existing stabilizing rod.

2. An orthopaedic fixation system, comprising:
   a bone anchor having proximal and distal ends; and
   an elbow having portion that engages with the bone anchor once in position and an arm that engages with an existing stabilizing rod.

3. The orthopaedic fixation system of claim 2, wherein the bone anchor includes outwardly advancing tangs or barbs to assist with fixation.

4. The orthopaedic fixation system of claim 2, wherein the proximal end of the bone anchor is substantially at the surface of a bone once in position.

5. The orthopaedic fixation system of claim 2, wherein an existing stabilizing rod is generally transverse to the arm.

* * * * *